(12) United States Patent
Izallalen et al.

(10) Patent No.: US 9,267,106 B2
(45) Date of Patent: Feb. 23, 2016

(54) METHOD FOR INCORPORATION OF RECOMBINANT DNA

(75) Inventors: Mounir Izallalen, Savoy, IL (US); Steve Stoddard, Cerro Gordo, IL (US)

(73) Assignee: Eastman Renewable Materials, LLC, Kingsport, TN (US)

( * ) Notice: Subject to any disclaimer, the term of this patent is extended or adjusted under 35 U.S.C. 154(b) by 199 days.

(21) Appl. No.: 13/368,483

(22) Filed: Feb. 8, 2012

(65) Prior Publication Data

US 2012/0208281 A1    Aug. 16, 2012

Related U.S. Application Data

(60) Provisional application No. 61/442,588, filed on Feb. 14, 2011.

(51) Int. Cl.
| | | |
|---|---|---|
| *C12N 15/74* | (2006.01) | |
| *C12N 1/20* | (2006.01) | |
| *C12N 9/10* | (2006.01) | |
| *C12N 9/16* | (2006.01) | |

(52) U.S. Cl.
CPC ............... *C12N 1/20* (2013.01); *C12N 9/1007* (2013.01); *C12N 9/16* (2013.01); *C12N 15/74* (2013.01); *C12Y 301/03016* (2013.01)

(58) Field of Classification Search
None
See application file for complete search history.

(56) References Cited

U.S. PATENT DOCUMENTS

| | | |
|---|---|---|
| 6,280,721 B1 | 8/2001 | Adams et al. |
| 2009/0047718 A1 | 2/2009 | Blaschek et al. |
| 2009/0305369 A1 | 12/2009 | Donaldson et al. |
| 2010/0075424 A1 | 3/2010 | Tracy et al. |
| 2010/0330678 A1 | 12/2010 | Soucaille |
| 2011/0230682 A1 | 9/2011 | Schmalisch et al. |
| 2011/0281313 A1 | 11/2011 | Wach et al. |

FOREIGN PATENT DOCUMENTS

| | | |
|---|---|---|
| EP | 2267126 | 12/2010 |
| WO | WO2006130925 | 12/2006 |
| WO | WO2008040387 | 4/2008 |
| WO | WO2008144060 | 11/2008 |
| WO | WO2010069542 | 6/2010 |
| WO | WO2010084349 | 7/2010 |
| WO | WO2012035420 | 3/2012 |

OTHER PUBLICATIONS

Clark, et al., "Isolation and Characterization of Mutants of Clostridium acetobutylicum ATCC 824 Deficient in Acetoacetyl-Coenzyme A: Acetate/Butyrate:Coenzyme A-Transferase (EC 2.8.3.9) and in Other Solvent Pathway Enzymes", Applied and Environmental Microbiology, Apr. 1989, vol. 55, No. 4, pp. 970-976.

Durre, et al., "Transcriptional Regulation of Solventogenesis in Clostridium acetobutylicum", J. Mol. Microbiol. Biotechnology, 2002, vol. 4, No. 3, pp. 295-300.

Harris, et al., "Northern, Morphological, and Fermentation Analysis of spo0A Inactivation and Overexpression in Clostridium acetobutylicum ATCC 824", Journal of Bacteriology, Jul. 2002, vol. 184, No. 13, pp. 3586-3597.

Heap, et al., "ClosTron-targeted mutagenesis", Methods Mol Biol, 2010, vol. 646, 165-82 (Abstract).

Heap, et al., "The ClosTron: A universal gene knock-out system for the genus *Clostridium*", Journal of Microbiological Methods, 2007, vol. 70, pp. 452-464.

Jones, et al., "Actone-Butanol Fermentation Revisited" Microbiological Reviews, Dec. 1986, vol. 50, No. 4, pp. 484-524.

Lee, et al., "Vector Construction, Transformation, and Gene Amplification in Clostridium acetobutylicum ATCC 824a", Annals New York Academy of Science, 1992, vol. 665, pp. 39-51.

Liu S et al: "Functional expression of the thiolase gene thl from Clostridium beijerinckii P260 in Lactococcus lactis and Lactobacillus buchneri", New Biotechnology, Elsevier BV, NL, vol. 1 . 27, No. 4, Sep. 30, 2010, pp. 283-288, XP027171907, ISSN: 1871-6784 [retrieved on Jul. 22, 2010] cited in the application abstract.

Mermelstein, et al., "In Vivo Methylation in *Escherichia coli* by the Bacillus subtilis Phage F 3T I Methyltransferase to Protect Plasmids from Restriction upon Transformation of Clostridium acetobutylicum ATCC 824", Applied and Environmental Microbiology, Apr. 1993, vol. 59, No. 4, pp. 1077-1081.

PCT Intl Search Report for Application PCT/US12/24813 (corresponding to U.S. Appl. No. 13/368,506), Intl fiing date Feb. 13, 2012, mailed Aug. 31, 2012, 8 pages.

Petersen, et al., "Molecular Cloning of an Alcohol (Butanol) Dehydrogenase Gene Cluster from Clostridium acetobutylicum ATCC 824", Journal of Bacteriology, Mar. 1991, vol. 173, No. 5, pp. 1831-1834.

Ramanu, "Optimization of the Electrotransformation efficiency of Clostridium Beijerinickii BA101", Thesis submitted at the Graduate College of the University of Illinios at Urbana-Champaign, 2006, 96 pages.

Rogers et al: "Clostridium acetobutylicum Mutants That Produce Butyraldehyde and Altered Quantities of Solvents.", Applied and Environmental Microbiology, vol. 53, No. 12, Dec. 1, 1987, pp. 2761-2766, XP55021139, ISSN: 0099-2240 the whole document.

Sambrook et al., "Molecular Cloning: A Laboratory Manual", Cold Spring Harbor Laboratory Press, 3rd Edition, 2001, pp. 1.24-1.28.

Scotcher, "Genetic Factors Affecting the Regulation of Solventogenesis in Clostridium acetobutylicum ATCC824" Thesis submitted at the Rice University in Houston Texas, Jan. 2005, Abstract, 245 pages.

Scotcher, et al., "SpoIIE Regulates Sporulation but Does Not Directly Affect Solventogenesis in Clostridium acetobutylicum ATCC 824", Journal of Bacteriology, Mar. 2005, vol. 187, No. 6, pp. 1930-1936.

(Continued)

Primary Examiner — Nancy T Vogel
(74) Attorney, Agent, or Firm — Lee & Hayes, PLLC

(57) ABSTRACT

The invention provides methods of preparing bacteria of interest with a stably integrated nucleic acid sequence of interest.

18 Claims, 1 Drawing Sheet

(56) References Cited

OTHER PUBLICATIONS

Figure 1A:
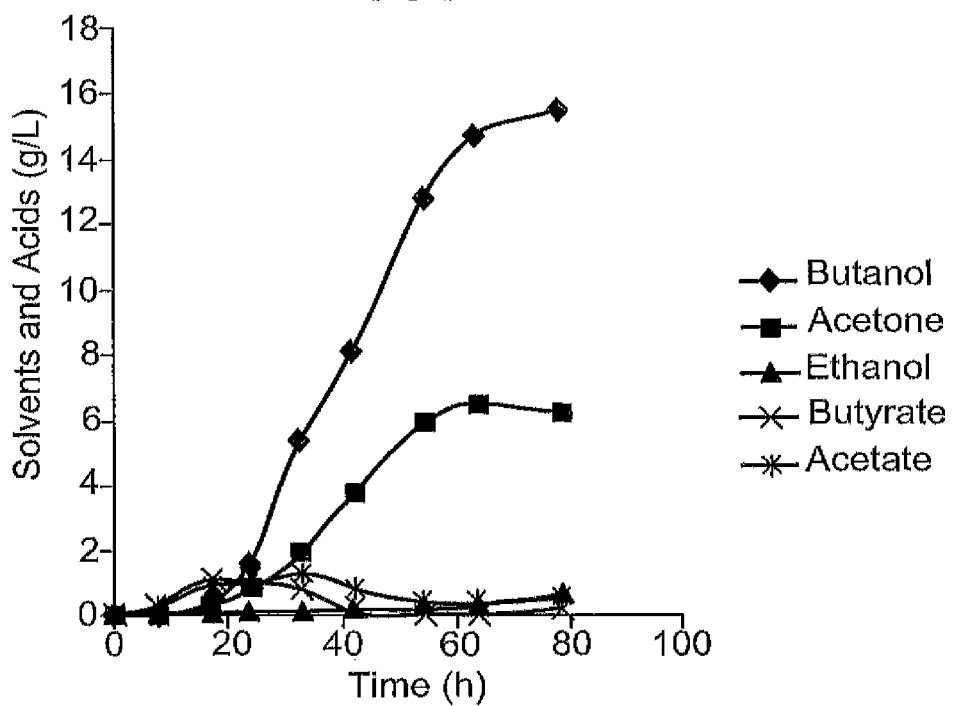

Tracy, et al., "Inactivation of sE and sG in Clostridium acetobutylicum illuminates their roles in clostridial-cell form biogenesis, granulose synthesis, solventogenesis, and spore morphogenesis", JB Accepts published online ahead of print on Jan. 7, 2011, pp. 1-52.

Tummala, et al., "Antisense RNA Downregulation of Coenzyme a Transferase Combined with Alcohol-Aldehyde Dehydrogenase Overexpression Leads to Predominantly Alcohologenic Clostridium acetobutylicum Fermentations", Journal of Bacteriology, Jun. 2003, vol. 185, No. 12, pp. 3644-3653.

Wolfsberg, et al., "Sequence Similarity Searching Using the Blast FAmily of Programs", Current Protocols in Molecular Biology, 1999, Unit 19.3, pp. 19.3.1-19.3.29.

Guss, et al., "Dcm methylation is detrimental to plasmid transformation in Clostridium thermocellum", Biotechnology for Biofuels, Vo.. 5, No. 1, May 1, 2012, pp. 30-30.

Klapatch, et al., "Restriction endonucleus activity in Clostridium thermocellum and Clostridium thermosaccharolyticum", Applied Microbiology and Biotechnology, Springer Verlag, Berlin, DE, vol. 45, No. 1-2, Jan. 1, 1996, pp. 127-131.

Macaluso, et al., "Efficient transformation of Bacillus thuringiensis requires nonmethylated plasmid DNA", Journal of Bacteriology, vol. 173, No. 3, Feb. 1, 1991, pp. 1353-1356.

MacNeil, et al., "Characterization of a Unique Methyl-Specific Restriction System in Streptomyces avermitilis", Journal of Bacteriology, American Society for Microbiology, Washington, DC, US, vol. 170, No. 12, Jan. 1, 1988, pp. 5607-5612.

Palmer, et al., "The dam and dcm strains of *Escherichia coli*—a review", Gene, Elsevier, Amsterdam, NL, vol. 143, No. 1, Jay 27, 1994, pp. 1-12.

PCT Search Report mailed Sep. 19, 2012 for PCT application No. PCT/US2012/024833, 22 pages.

Ramanu, et al., "Impact of methylation state of plasmid on transformability of Clostridium beijerinckii BA101", Abstracts of the General Meeting of the American Society for Microbiology, Washington, US, vol. 106, May 25, 2006, p. 292.

Alsaker, et al., "Transcriptional Program of Early Sporulation and Stationary-Phase Events in Clostridium acetobutylicum"Journal of Bacteria; Oct. 2005; vol. 187, No. 20; pp. 7103-7118.

Altschul, et al., "Gapped BLAST and PSI-BLAST: a new generation of protein database search programs", Nucleic Acids research, 1997, vol. 25, No. 17, pp. 3389-3402.

Atsumi, et al., "Direct photosynthetic recycling of carbon dioxide to isobutyraldehyde", Nature Biotechnology, Dec. 2009, vol. 27, No. 12, pp. 1177-1182.

Ausubel et al., "Current Protocols in Molecular Biology", John Wiley & Sons, Inc., 2001, Unit 15.0.1-15.8.20.

Oksana V Berezina et al: "Reconstructing the clostridial n-butanol metabolic pathway in Lactobaci 11 us brevis", Applied Microbiology and Biotechnology, Springer, Berlin, DE, vol. 87, No. 2, 2 March 2818 (2818-83-82), pp. 635-646, XP819841589, ISSN: 1432-8614 abstract, 2010.

Cooksley, et al.,"Targeted Mutagenesis of the Clostridiumacetobutylicum Acetone-Butanol-Ethanol Fermentation Pathway", Metabolic Engineering, vol. 14, 2012, pp. 630-641.

Pyne, et al.,"Technical Guide for Genetic Advancement of Underdeveloped and Intractable Clostridium", Biotechnology Advances, vol. 32, 2014, pp. 623-641.

Wang, et al.,"Development of a Gene Knockout System Using Mobile Group II Introns (Targetron) and Genetic Disruption of Acid Production Pathways in Clostridium beijerinckii", AEM, vol. 79, No. 19, 2013, pp. 5853-5863.

SEQUENCE LISTING

```
<160> NUMBER OF SEQ ID NOS: 10

<210> SEQ ID NO 1
<211> LENGTH: 18
<212> TYPE: DNA
<213> ORGANISM: Clostridium beijerinckii

<400> SEQUENCE: 1
tgaggcgagc taatgtgc                                                18

<210> SEQ ID NO 2
<211> LENGTH: 17
<212> TYPE: DNA
<213> ORGANISM: Clostridium beijerinckii

<400> SEQUENCE: 2
ggtgctgcgc ctatctt                                                 17

<210> SEQ ID NO 3
<211> LENGTH: 30
<212> TYPE: DNA
<213> ORGANISM: Clostridium beijerinckii

<400> SEQUENCE: 3
atgcgatatc ataagactta gaagcaaact                                   30

<210> SEQ ID NO 4
<211> LENGTH: 33
<212> TYPE: DNA
<213> ORGANISM: Clostridium beijerinckii

<400> SEQUENCE: 4
atgcagatat cactcataga attatttcct ccc                               33

<210> SEQ ID NO 5
<211> LENGTH: 22
<212> TYPE: DNA
<213> ORGANISM: Clostridium beijerinckii

<400> SEQUENCE: 5
ttaagccaag aaaatcggag aa                                           22

<210> SEQ ID NO 6
<211> LENGTH: 20
```

```
<212> TYPE: DNA
<213> ORGANISM: Clostridium beijerinckii

<400> SEQUENCE: 6
gtcagacgca tggctttcaa                                               20

<210> SEQ ID NO 7
<211> LENGTH: 24
<212> TYPE: DNA
<213> ORGANISM: Clostridium beijerinckii

<400> SEQUENCE: 7
tatcaccagg tcgtagcact tctc                                          24

<210> SEQ ID NO 8
<211> LENGTH: 22
<212> TYPE: DNA
<213> ORGANISM: Clostridium beijerinckii

<400> SEQUENCE: 8
acttacccgc cataccacag at                                            22

<210> SEQ ID NO 9
<211> LENGTH: 24
<212> TYPE: DNA
<213> ORGANISM: Clostridium beijerinckii

<400> SEQUENCE: 9
tatccgcctc catccagtct atta                                          24

<210> SEQ ID NO 10
<211> LENGTH: 24
<212> TYPE: DNA
<213> ORGANISM: Clostridium beijerinckii

<400> SEQUENCE: 10
ctgctatgtg gcgcggtatt atcc                                          24
```

METHOD FOR INCORPORATION OF RECOMBINANT DNA

CROSS REFERENCE TO RELATED APPLICATION

This application claims the benefit of U.S. Provisional Application Ser. No. 61/442,588, filed Feb. 14, 2011, which is incorporated herein by reference in its entirety.

SEQUENCE LISTING

The following application contains a sequence listing in computer readable format (CRF), submitted as a text file in ASCII format. The content of the CRF is hereby incorporated by reference.

BACKGROUND OF THE INVENTION

The presence of a restriction-modification (RM) system represents a barrier for the transformation of bacteria with recombinant DNA. This is especially applicable to *Clostridia* sp. The recalcitrance of *Clostridia* to accept foreign DNA is caused by the presence of a potent restriction system, especially the type II restriction endonucleases.

The first breakthrough in the genetic engineering of *Clostridia* was the modification of transforming DNA with a phage methyltransferase to protect transforming DNA from digestion before electroporation into *C. acetobutylicum* ATCC 824 (see, e.g., Lee et al., *Ann. NY Acad. Sci.*, 665: 39-51 (1992)). Since then, methylation of DNA prior to transforming *Clostridia* has become a standard procedure (see, e.g., Mermelstein et al., *App. Environ. Microbiol.*, 59: 1077-1081 (1993); and Tardif et al., *J. Ind. Microbiol. Biotechnol.*, 27: 271-274 (2001))). Although plasmid DNA could be introduced into *Clostridia*, the transformation efficiency was very low. As a consequence, gene knockout via homologous recombination mechanisms using non-replicative plasmids or linear DNA was very tedious to achieve. The difficulty of targeted gene disruption in solventogenic *Clostridia* is well illustrated by the low number of mutants published to date.

More recent techniques that rely on anti-sense RNA technology (Scotcher et al., *J. Bacteriol.*, 187: 1930-1936 (2005)) or group II intron (Heap et al., *J. Microbiol. Methods*, 70: 452-464 (2007)) are very complex and still necessitate methylating the transforming DNA a priori.

There remains a desire for an improved method for stably integrating a nucleic acid sequence of interest into bacteria, especially *Clostridia*.

BRIEF SUMMARY OF THE INVENTION

The invention provides a method of providing bacteria of interest with a stably integrated nucleic acid sequence of interest, which method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, (c) isolating the nucleic acid molecule from the propagated dcm⁻ bacteria, and (d) transforming bacteria of interest with the isolated nucleic acid molecule, thereby providing bacteria of interest with a stably integrated nucleic acid sequence of interest.

The invention also provides a method of providing bacteria of interest with a stably integrated nucleic acid sequence of interest, which method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, and (c) bringing the propagated dcm⁻ bacteria and bacteria of interest into contact with each other, thereby providing bacteria of interest with a stably integrated nucleic acid sequence of interest.

The invention provides a method of providing bacteria of interest with a stably integrated nucleic acid sequence of interest, which method comprises (a) transforming bacteria of interest with a nucleic acid molecule comprising a nucleic acid sequence of interest, wherein the nucleic acid sequence of interest comprises at least one region of identity with the genome of the bacteria of interest and a first selection marker, thereby providing (1) bacteria of interest that do not contain the nucleic acid molecule and (2) bacteria of interest that contain the nucleic acid molecule, (b) culturing the bacteria of interest of step (a) under conditions that increase the concentration of the bacteria of interest that contain the nucleic acid molecule, wherein the bacteria of interest that contain the nucleic acid molecule include (1) bacteria of interest into which the nucleic acid molecule has been stably integrated into the genome of the bacteria of interest and (2) bacteria of interest into which the nucleic acid molecule has not been stably integrated into the genome of the bacteria of interest, and (c) culturing the bacteria of interest of step (b) under conditions that increase the proportion of the bacteria of interest into which the nucleic acid molecule has been stably integrated into the genome of the bacteria of interest.

Additionally, the invention provides a method of providing bacteria of interest with a stably integrated nucleic acid sequence of interest, which method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, (c) isolating the nucleic acid molecule from the propagated dcm⁻ bacteria, (d) transforming the bacteria of interest with the isolated nucleic acid molecule, thereby providing (1) bacteria of interest that do not contain the nucleic acid molecule and (2) bacteria of interest that contain the nucleic acid molecule, (e) culturing the bacteria of interest of step (d) under conditions that increase the concentration of the bacteria of interest that contain the nucleic acid molecule, wherein the bacteria of interest that contain the nucleic acid molecule include (1) bacteria of interest into which the nucleic acid molecule has been stably integrated into the genome of the bacteria of interest and (2) bacteria of interest into which the nucleic acid molecule has not been stably integrated into the genome of the bacteria of interest, and (f) culturing the bacteria of interest of step (e) under conditions that increase the proportion of the bacteria of interest into which the nucleic acid molecule has been stably integrated into the genome of the bacteria of interest.

The invention further provides a method of providing bacteria of interest with a stably integrated nucleic acid sequence of interest, which method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, (c) bringing the propagated dcm⁻ bacteria and bacteria of interest into contact with each other, thereby providing (1) bacteria of interest that do not contain the nucleic acid molecule and (2) bacteria of interest that contain the nucleic acid molecule, (d) culturing the bacteria of interest of step (c) under conditions that increase the concentration of the bacteria of interest that contain the nucleic acid molecule, wherein the bacteria of interest that contain the nucleic acid molecule include (1) bacteria of interest into which the nucleic acid molecule has been stably integrated into the genome of the bacteria of interest and (2) bacteria of interest into which the nucleic acid molecule has not been stably integrated into the genome of the bacteria of interest, and (e) culturing the bacteria of interest of step (d) under conditions that increase the proportion of the bacteria of interest into which the nucleic acid molecule has been stably integrated into the genome of the bacteria of interest.

BRIEF DESCRIPTION OF THE SEVERAL VIEWS OF THE DRAWING(S)

Figure 1B:
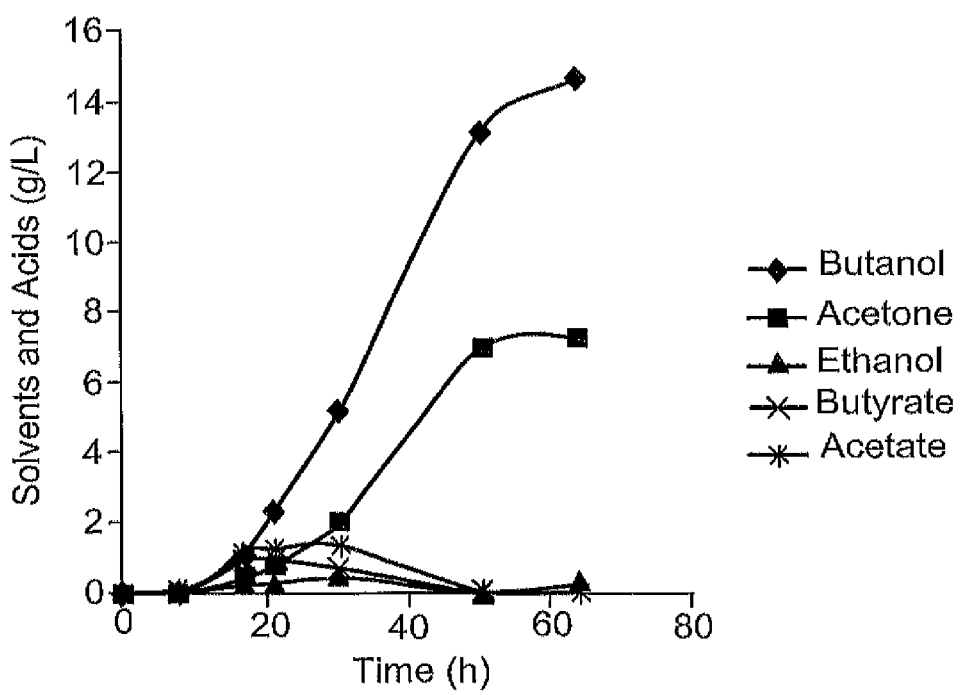

FIGS. 1A and 1B are graphs depicting the solvent and acid production profile by the parent *C. beijerinckii* BA101 (A) and SPOIIE mutant *C. beijerinckii* ΔspoIIE strain TVS240 (B). Time (hours) is on the x-axis, and the concentration of the solvents and acids (g/L) is on the y-axis. Results for butanol (◇), acetone (□), ethanol (Δ), butyrate (x), and acetate (*) are depicted.

DETAILED DESCRIPTION OF THE INVENTION

The invention provides methods of preparing bacteria of interest with a stably integrated nucleic acid sequence of interest.

In a first embodiment, the method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, (c) isolating the nucleic acid molecule from the propagated dcm⁻ bacteria, and (d) transforming bacteria of interest with the isolated nucleic acid molecule, thereby providing bacteria of interest with a stably integrated nucleic acid sequence of interest.

In a second embodiment, the method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, and (c) bringing the propagated dcm⁻ bacteria and bacteria of interest into contact with each other to allow the transfer of the nucleic acid molecule of interest by conjugation, thereby providing bacteria of interest with a stably integrated nucleic acid sequence of interest.

The inventors surprisingly discovered that when a nucleic acid molecule comprising a nucleic acid of interest was prepared in a dcm⁻ bacterium, the nucleic acid sequence of interest could be more easily integrated into the genome of a bacteria of interest, wherein the bacteria of interest has a potent restriction and modification (RM) system. dcm⁻ bacteria produce little or no dcm methylase, which is an enzyme that methylates the $C^5$ position of cytosine in the sequences CCAGG and CCTGG. While not wishing to be bound by any particular theory, preparing the nucleic acid molecule in a dcm⁻ bacterium allows the nucleic acid molecule to evade the RM system of bacteria into which the nucleic acid sequence of interest is to be integrated, as well as increases the chances of homologous recombination occurring between the nucleic acid sequence of interest and the bacteria with the RM system.

The bacteria of interest can be any suitable bacteria. In one embodiment, the bacteria of interest is recalcitrant to genetic manipulation (e.g., due to a potent RM system). Examples of bacteria that are recalcitrant to genetic manipulation are known in the art and include, for example, *Pelobacter carbinolicus*, *Pelobacter propionicus*, and bacteria from *Clostridia* sp., such as *C. difficile*, *C. botulinum*, *C. tetani*, *C. beijerinckii*, *C. acetobutylicum*, *C. saccharobutylicum*, *C. saccharobutylacetonicum*, *C. thermocellum*, *C. phytofermentens*, *C. carboxidivorans*, *C. ragsdalei*, *C. ljungdahli*, *C. autoethanogemum*, *C. cellulolyticum*, *C. sporogenes*, and *C. butyricum*. Preferably, the bacteria of interest is *C. beijerinckii*, such as *C. beijerinckii* NCIMB 8052 and the mutant strain BA101.

The dcm⁻ bacterium can be any suitable bacterium. Preferably, the dcm⁻ bacterium is from a different species than the bacteria of interest. A non-limiting example is *E. coli*. In one embodiment, the dcm⁻ bacterium is dam⁺. The methylase encoded by the dam gene (dam methylase) transfers a methyl group from S-adenosylmethionine to the $N^6$ position of the adenine residue in the sequence GATC.

The nucleic acid molecule comprising a nucleic acid sequence of interest can be any suitable nucleic acid molecule. For example, the nucleic acid molecule can be linear DNA or a nucleic acid vector, such as a plasmid or a viral vector (e.g., bacteriophage).

The nucleic acid sequence of interest comprises at least one region of identity with the genome of the bacteria of interest and a first selection marker. In one embodiment, the nucleic acid sequence of interest comprises a first region of identity with the genome of the bacteria of interest and a second region of identity with the genome of the bacteria of interest. In this embodiment, the first selection marker can be positioned in any suitable location relative to the first and second regions of identity; however, in a preferred embodiment, the first selection marker is positioned between the first and second regions of identity.

In a second embodiment, the nucleic acid sequence of interest comprises a first region of identity with the genome of the bacteria of interest, a second region of identity with the genome of the bacteria of interest, a first selection marker, and nucleic acid sequence/gene encoding a polypeptide of interest (e.g., an enzyme in metabolic pathway).

In the first and second embodiments, the first and second regions of identity can be any suitable length. For example, suitable lengths of the first and second regions of identity include, but are not limited to, about 100 bp to about 30,000 bp (e.g., at least 500 bp, at least 1,000 bp, at least 2,000 bp, at least 5,000 bp, at least 10,000 bp, and at least 20,000 bp).

In an alternative embodiment, the nucleic acid sequence comprises one large region of identity. The region of identity can be any length suitable to drive integration into the genome of the bacteria of interest and interruption of gene expression. Suitable lengths of the region of identity include, but are not limited to, about 100 bp to about 30,000 bp (e.g., at least 500 bp, at least 1,000 bp, at least 2,000 bp, at least 5,000 bp, at least 10,000 bp, and at least 20,000 bp).

The nucleic acid molecule also can comprise a second selection marker. The second selection marker can be used to select for double homologous recombination events resulting in plasmid excision and allelic replacement.

The first and second selection markers can be any suitable selection markers. Suitable selection markers include, but are not limited to, antibiotic resistance genes and metabolic markers. Suitable antibiotic resistance genes include resistance genes to erythromycin (erm), ampicillin (bla), kanamycin (kan), chloramphenicol (cat), spectinomycin (aadA), and tetracycline (tet). Suitable metabolic markers include genes that complement nutritional auxotrophies in minimal media, such as purA (adenylosuccinate synthetase) or asd (aspartate semi-aldehyde dehydrogenase) in a bacterial strain that cannot synthesize adenine or diaminopimelic acid, respectively.

Additionally or alternatively, the nucleic acid molecule can comprise at least one fluorescent tag, chromogenic tag, or a combination thereof. Examples of fluorescent and chromogenic tags include, but are not limited to, green fluorescent protein (GFP), red fluorescent protein (RFP), yellow fluorescent protein (YFP), β-glucuronidase, and β-galactosidase.

The nucleic acid molecule further can comprise an origin of replication that is functional in the dcm$^-$ bacterium (e.g., $E.$ $coli$), an origin of replication that is functional in the bacteria of interest (e.g., $Clostridia$ sp.), or a combination thereof.

The nucleic acid sequence of interest can contain functional genes that confer new properties for the bacteria of interest, such as genes encoding one or more enzymes involved in the production of solvents (e.g., n-butanol, ethanol, butyrate, acetate, and acetone) or precursors thereof (e.g., n-butyraldehyde).

Additionally or alternatively, the nucleic acid sequence of interest can contain a mutagenic region that can eliminate gene function by means of integration, such as by removing metabolic or regulatory pathways that compete with solvent production. An example of the implementation of a gene modification that could positively impact solvent production is the inhibition of sporulation by knocking out genes involved in this process. Therefore, in one aspect, the first and second regions of identity are derived from a spoIIE gene, such as a spoIIE gene from $C.$ $beijerinckii$, wherein the incorporation of the nucleic acid sequence of interest results in a decrease in SpoIIE expression and/or function.

In another aspect, butanol dehydrogenase expression and/or function is reduced or knocked-out in a butanologenic organism (e.g., butanologenic $Clostridia$, such as $C.$ $acetobutylicum$, $C.$ $beijerinckii$, $C.$ $saccharobutylicum$, and $C.$ $saccharobutylacetonicum$) so as to enhance production of n-butyraldehyde. In a particular embodiment, the first and second regions of identity are derived from a gene encoding butanol dehydrogenase, such as the butanol dehydrogenase (bdh) gene from $C.$ $beijerinckii$, wherein the incorporation of the nucleic acid sequence of interest results in a decrease in bdh expression and/or function.

In another embodiment, the method of providing bacteria of interest with a stably integrated nucleic acid sequence of interest comprises (a) transforming bacteria of interest with a nucleic acid molecule comprising a nucleic acid sequence of interest, wherein the nucleic acid sequence of interest comprises at least one region of identity with the genome of the bacteria of interest and a first selection marker, thereby providing (1) bacteria of interest that do not contain the nucleic acid molecule and (2) bacteria of interest that contain the nucleic acid molecule, (b) culturing the bacteria of interest of step (a) under conditions that increase the concentration of the bacteria of interest that contain the nucleic acid molecule, wherein the bacteria of interest that contain the nucleic acid molecule include (1) bacteria of interest into which the nucleic acid molecule has been stably integrated into the genome of the bacteria of interest and (2) bacteria of interest into which the nucleic acid molecule has not been stably integrated into the genome of the bacteria of interest, and (c) culturing the bacteria of interest of step (b) under conditions that increase the proportion of the bacteria of interest into which the nucleic acid molecule has been stably integrated into the genome of the bacteria of interest. The method further can comprise (d) culturing the bacteria of interest of step (c) under conditions to decrease the concentration of any residual bacteria of interest that do not contain the nucleic acid molecule and/or comparing the resulting culture of step (b), (c), and/or (d) with a the resulting culture of an identical method except that the nucleic sequence of interest of the bacteria of interest does not contain at least one region of identity with the genome of the bacteria of interest.

While not wishing to be bound by any particular theory, it appears that culturing the bacteria of interest under selective conditions followed by non-selective conditions results in increased loss of the bacteria in which the nucleic acid molecule has not been stably integrated into the genome of the bacteria of interest (e.g., still maintained as a plasmid). Thus, the inclusion of the non-selective culturing step in the inventive methods enriches for (i.e., increases the proportion of) the bacteria of interest into which the nucleic acid molecule has been stably integrated into the genome of the bacteria of interest. The non-selective culturing step can be performed using any suitable technique known in the art. Preferably, the non-selective culturing step is performed using serial replica plating. In serial replica plating, an isolate repeatedly (e.g., 2, 3, 4, 5, 6, 7, 8, 9, or more times) is transferred from one substrate to another (e.g., agar plate) in an effort to dilute and enrich for individual bacterial clones of interest.

This non-selective culturing step can be followed by a step of culturing the bacteria of interest under selective conditions in order to further decrease the concentration of any residual bacteria of interest that do not contain the nucleic acid molecule (e.g., wherein the nucleic acid sequence of interest is not integrated into the genome of the bacteria of interest or maintained as plasmid).

These steps can be in addition to or as an alternative to those described above. When the steps are in addition to the above-described steps, in a first aspect, the inventive method comprises (a) providing a dcm$^-$ bacterium containing a nucleic acid molecule comprising a nucleic acid sequence of interest, wherein the nucleic acid sequence of interest comprises at least one region of identity with the genome of bacteria of interest and a first selection marker, and wherein the dcm$^-$ bacterium and the bacteria of interest are of different species, (b) propagating the dcm$^-$ bacterium, (c) isolating the nucleic acid molecule from the propagated dcm$^-$ bacteria, (d) transforming the bacteria of interest with the isolated nucleic acid molecule, thereby providing (1) bacteria of interest that do not contain the nucleic acid molecule and (2) bacteria of interest that contain the nucleic acid molecule, (e) culturing the bacteria of interest of step (d) under conditions that increase the concentration of the bacteria of interest that contain the nucleic acid molecule, wherein the bacteria of interest that contain the nucleic acid molecule include (1) bacteria of interest into which the nucleic acid molecule has been stably integrated into the genome of the bacteria of interest and (2) bacteria of interest into which the nucleic acid molecule has not been stably integrated into the genome of the bacteria of interest, and (f) culturing the bacteria of interest of step (e) under conditions that increase the proportion of the bacteria of interest into which the nucleic acid molecule has been stably integrated into the genome of the bacteria of interest. The method of the first aspect further can comprise a step of culturing the bacteria of interest of step (e) under conditions to decrease the concentration of any residual bacteria of interest that do not contain the nucleic acid molecule.

In a second aspect, the inventive method comprises (a) providing a dcm⁻ bacterium containing a nucleic acid molecule comprising a nucleic acid sequence of interest, wherein the nucleic acid sequence of interest comprises at least one region of identity with the genome of bacteria of interest and a first selection marker, and wherein the dcm⁻ bacterium and the bacteria of interest are of different species, (b) propagating the dcm⁻ bacterium, (c) bringing the propagated dcm⁻ bacteria and bacteria of interest into contact with each other, thereby providing (1) bacteria of interest that do not contain the nucleic acid molecule and (2) bacteria of interest that contain the nucleic acid molecule, (d) culturing the bacteria of interest of step (c) under conditions that increase the concentration of the bacteria of interest that contain the nucleic acid molecule, wherein the bacteria of interest that contain the nucleic acid molecule include (1) bacteria of interest into which the nucleic acid molecule has been stably integrated into the genome of the bacteria of interest and (2) bacteria of interest into which the nucleic acid molecule has not been stably integrated into the genome of the bacteria of interest, and (e) culturing the bacteria of interest of step (d) under conditions that increase the proportion of the bacteria of interest into which the nucleic acid molecule has been stably integrated into the genome of the bacteria of interest. The method of the second aspect further can comprise a step of culturing the bacteria of interest of step (f) under conditions to decrease the concentration of any residual bacteria of interest that do not contain the nucleic acid molecule.

The following examples further illustrate the invention but, of course, should not be construed as in any way limiting its scope.

EXAMPLE 1

This example describes exemplary experimental conditions for the inventive methods.
Preparation of Plasmids Before transforming a recipient *Clostridium beijerinckii* BA101, plasmid DNA was prepared from a dcm⁻ derivative of *E. coli* (GM30). The DNA methylation profile of the plasmid DNA was verified by restriction digestion with restriction enzyme pspGI, which does not digest dcm⁻ DNA. The plasmid DNA contained an origin of replication that is functional in *E. coli* and an origin of replication that is functional in *Clostridium* sp. The two plasmids tested were pMTL500E, a pAM□1 derivative plasmid, and pGLE a pIM13 derivative plasmid. Both plasmids confer resistance to ampicillin (amp) and erythromycin (erm) that were used for selection in *E. coli* and *C. beijerinckii*, respectively.
Preparation of Electrocompetent Cells Electrocompetent cells were prepared by germinating spores of *C. beijerinckii* BA101 in TGY broth (tryptone 30 g/L, glucose 20 g/L, yeast extract 10 g/L, and L-cystein 1 g/L) overnight. The cells then were propagated on 100 mL of P2YE (glucose 60 g/L, yeast extract 1 g/L, 1 mL buffer solution (KH$_2$PO$_4$ 50 g/L, K$_2$HPO$_4$, and ammonium acetate 200 g/L), 1 mL vitamin stock solution (Para-amino-benzoic acid 0.1 g/L, thiamine 0.1 g/L, and biotin 0.001 g/L), and 1 mL of mineral stock solution (MgSO$_4$.7H$_2$O 20 g/L, MnSO$_4$.H$_2$O 1 g/L, FeSO$_4$.7H$_2$O 1 g/L, and NaCl 1 g/L) for 5 hours to reach an absorbance at optical density (OD) 600 nm in the range of 0.8 to 1.0. Cells were washed twice with an equal volume of electroporation buffer (sucrose 0.3 M). Electrocompetent cells were resuspended in 3 mL of the electroporation buffer.
Electroporation The suspension of electrocompetent cells (400 µL) was mixed with 1 µg of plasmid DNA in an electroporation cuvette (0.4 cm gap) and left on ice for 5 minutes. Electroporation was carried out using a Bio-Rad Gene-Pulser electroporator equipped with a pulse controller with the following electrical settings: voltage of 1.5 kV, resistance of 400 □, and capacitance of 25 µF. The cells were transferred to 10 mL of anaerobic TGY medium and then incubated for recovery at 33° C. for 5 hours.
Selection After recovery, the cell culture was plated on TGY plates containing erm (35 µg/mL). Plates were incubated under an anaerobic atmosphere of 95% N$_2$ and 5% H$_2$. Positive transformants typically form colonies in approximately 36 hours for pMTL500E and 2 days for pGLE plasmids.

EXAMPLE 2

This method describes the use of the inventive methods in the preparation of a spoIIE mutant strain.

To generate a mutagenic fragment of spoIIE, a portion of spoIIE gene from *C. beijerinckii* NCIMB 8052 (cbei_0097) was amplified using the forward primer pKO-Spo-fwd 5'-TGAGGCGAGCTAATGTGC-3' (SEQ ID NO: 1) and the reverse primer pKO-spo-Rev 5'-GGTGCTGCGCCTATCTT-3' (SEQ ID NO: 2). These two primers amplify a portion of the spoIIE gene from residues 2 to 2090.

The PCR product was cloned in the pCR 2.1-TOPO vector (Invitrogen, Carlsbad, Calif.) to generate plasmid pSpo2K. The internal fragment of spoIIE was removed by digesting pSpo2K with NdeI and BstZI.

The gene providing erythromycin resistance was generated from pMTL500E using the forward primer ErmB-up-EcoRV 5'-ATGCGATATCATAAGACTTAGAAGCAAACT-3' (SEQ ID NO: 3) and the reverse primer ErmB-dwn-EcoRV 5'-ATGCAGATATCACTCATAGAATTATTTCCTCCC-3' (SEQ ID NO: 4). The PCR product was digested with EcoRV and ligated to the NdeI/BstZI digested and blunt-ended pSpo2K.

The new plasmid pSpo2k-erm4 was digested with kpnI and XbaI to release the mutagenic fragment composed of the 5' and 3' region of spoIIE separated by the ermB gene. The mutagenic fragment then was ligated to kpnI/XbaI-digested pGLE to produce pTMI26. The plasmid vector pTMI26 was transformed into a dcm⁻ *E. coli* strain as described in Example 1 to produce the unmethylated and mutagenic plasmid pTWJ1. pTWJ1 was electroporated into *Clostridium* following the same procedure and using the same electrical parameters as described in Example 1.

Purified colonies that are resistant to erythromycin were further confirmed by PCR using ErmB-up-EcoRV (SEQ ID NO: 3) and ErmB-dwn-EcoRV (SEQ ID NO: 4) to provide proof of the presence of the plasmid inside the cell. Positive colonies were cultivated in liquid media in the presence of antibiotic, and when they reached mid-log phase, they were spread on TGY plates containing erm (35 µg/mL). After overnight growth, the cells formed a bacterial lawn. At this point, plates were replica plated serially onto TGY without antibiotic. These steps were used to remove the selective pressure and enrich for cells that have lost the plasmid.

After 5 transfers, the cells were plated on TGY plates containing erm (35 µg/mL). This step was used to enrich for the cells that still have the resistance gene.

A strain transformed with the same kind of plasmid (pGLE) but without a mutagenic fragment was run in parallel. The absence of any region of identity in this plasmid prevents it from integrating the chromosome of the bacteria. This strain was used as a control to indicate when there is a high probability of the plasmid being lost. There was a greater probability that the plasmid carrying the mutagenic fragment integrated the chromosome when cultures of the control could not be recovered from the plates that have antibiotic while colonies from the mutagenized strain could still be isolated.

Confirmation of chromosomal integration at either the 5' or 3' region of identity was carried out by using pairs of primers where one primer attached to the antibiotic resistance gene and the other to a region outside the region of identity. Integrations at the 5' region were detected using a pair of primers composed of Up-int-sp1F 5'-TTAAGCCAAGAAAATCG-GAGAA-3' (SEQ ID NO: 5) that anneals to a region upstream of spoIIE and Up-int-sp1R 5'-GTCAGACGCATG-GCTTTCAA-3' (SEQ ID NO: 6) that anneals to the ermB gene. Integrations mediated by the 3' region of identity were detected using a pair of primers composed of Dwn-Int-spaltR 5'-TATCACCAGGTCGTAGCACTTCTCi-3' (SEQ ID NO: 7) located downstream the 3' region of homology and Dwn-int-sp1F 5'-ACTTACCCGCCATACCACAGAT-3' (SEQ ID NO: 8) located on the ermB gene.

The generation of PCR product with pairs that are specific for 5' or 3' integration detected mutants that have undergone single 5' or 3' mediated homologous recombination. Double homologous mutants generated a PCR product with both the 3' and the 5' specific primer pairs. Loss of plasmid was further confirmed by PCR directed against the bla gene present on the backbone of the plasmid using the primers bla-fwd 5'-TATC-CGCCTCCATCCAGTCTATTA-3' (SEQ ID NO: 9) and bla-rev 5'-CTGCTATGTGGCGCGGTATTATCC-3' (SEQ ID NO: 10). A particular isolate that is a double homologous mutant with loss of plasmid, designated spoIIE mutant strain TVS240, was isolated for further characterization.

To further confirm successful interruption of the spoIIE gene, microscopic images were captured of cells from the C. beijerinckii BA101 parent strain and the derivative spoIIE mutant strain TVS240 after 50 hours of fermentation in P2YE broth using standard procedures known in the art. After 50 hours of fermentation, the cells were well into the solventogenic stage. In the parent strain, the microscopic image contains numerous spores and endospores. In contrast, the mutant strain culture mainly was composed of cells in vegetative form with no apparent sign of spore formation.

To determine whether the non-sporulating mutant strain can still produce solvents/acids, the concentrations of butanol, acetone, ethanol, butyrate, and acetate were measured in the fermentation broth. Briefly, solvents and acids present in the culture supernatant were determined using a Hewlett-Packard/Agilent 6890 gas chromatograph equipped with a flame ionization detector and a J&W Scientific DB-FFAP column (30 m×0.250 mm capillary). The oven temperature was programmed from 40° C. to 230° C. at the rate of 50° C./min. The injector and detector temperatures were set at 230° C. and 250° C., respectively. Helium was the carrier gas and was set at 30 mL/min.

The solvent and acid production profiles by the C. beijerinckii BA101 parent strain and the ΔspoIIE mutant strain TVS240 are depicted in FIGS. 1A and 1B, respectively. A comparison of the solvent and acid production profiles depicted in FIGS. 1A and 1B reveals that the ΔspoIIE mutant strain TVS240 carried out solvent production to levels comparable to the parent strain. This result illustrates the uncoupling of sporulation and solvent production in the ΔspoIIE mutant strain TVS240.

EXAMPLE 3

This example describes that preparation of a recombinant Clostridia in which the expression of butanol dehydrogenase (bdh) is reduced or knocked-out.

To generate a mutagenic fragment of bdh, a portion of the bdh gene from Clostridia is amplified using primers that amplify a portion of the bdh gene. The PCR product is cloned in a vector, such as the pCR 2.1-TOPO vector (Invitrogen, Carlsbad, Calif.), to generate a plasmid (Plasmid 1) comprising the portion of the bdh gene.

The gene providing antibiotic resistance (e.g., erythromycin resistance from pMTL500E) is inserted into the portion of the bdh gene in Plasmid 1.

The resulting plasmid (Plasmid 2) is digested with the appropriate restriction enzymes to release the mutagenic fragment composed of the 5' and 3' region of bdh separated by the antibiotic gene. The mutagenic fragment then is ligated into a new plasmid (Plasmid 3), which is subsequently transformed into a dcm$^-$ E. coli strain as described in Example 1 to produce an unmethylated plasmid (Plasmid 4). Plasmid 4 is electroporated into Clostridium following the same procedure and using the same electrical parameters as described in Example 1.

Purified colonies that are resistant to the antibiotic are further confirmed by PCR to provide proof of the presence of the plasmid inside the cell. Positive colonies are cultivated in liquid media in the presence of antibiotic, and when the bacteria reach mid-log phase, the bacteria are spread on TGY plates containing erm (35 μg/mL). After overnight growth, the cells form a bacterial lawn. At this point, plates are replica plated serially onto TGY without antibiotic. These steps are used to remove the selective pressure and enrich for cells that have lost the plasmid.

After 5 transfers, the cells are plated on TGY plates containing erm (35 μg/mL). This step is used to enrich for the cells that still have the resistance gene.

A strain transformed with the same kind of plasmid but without a mutagenic fragment is run in parallel. The absence of any region of identity in this plasmid prevents it from integrating the chromosome of the bacteria. This strain is used as a control to indicate when there is a high probability of the plasmid being lost. There is a greater probability that the plasmid carrying the mutagenic fragment integrated the chromosome, when cultures of the control cannot be recovered from the plates that have antibiotic while colonies from the mutagenized strain could still be isolated.

Confirmation of chromosomal integration is carried out by using pairs of primers where one primer attached to the antibiotic resistance gene and the other to a region outside the region of identity. The generation of PCR product with primer pairs that are specific for 5' or 3' integration is indicative of the presence of mutants that have undergone single 5' or 3' mediated homologous recombination. Double homologous mutants generate a PCR product with both the 3' and the 5' specific primer pairs.

The resulting recombinant Clostridia is used, for example, to produce n-butyraldehyde.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of providing a *Clostridium* sp. of interest with a stably integrated nucleic acid sequence of interest, which method comprises:
providing a dcm− bacterium containing a plasmid comprising a nucleic acid sequence of interest, wherein the nucleic acid sequence of interest comprises at least one region of identity with a genome of the bacteria of interest and a first selection marker, and wherein the dcm− bacterium and the *Clostridium* sp. of interest are of different species,
propagating the dcm− bacterium,
isolating the plasmid from the propagated dcm−bacteria,
transforming the *Clostridium* sp. of interest with the isolated plasmid to produce transformed *Clostridium* sp. of interest, and
culturing the transformed *Clostridium* sp. of interest under selective conditions and under non-selective conditions to decrease the concentration of any residual *Clostridium* sp. of interest that do not contain the plasmid thereby providing *Clostridium* sp. of interest with a stably integrated nucleic acid sequence of interest,
wherein the plasmid is self-replicating in the dcm− bacterium and the *Clostridium* sp. of interest.

2. The method of claim 1, wherein the dcm− bacterium is a dcm− *E. coli* strain.

3. The method of claim 1, wherein the dcm− bacterium is dam+.

4. The method of claim 1, wherein the plasmid further comprises an origin of replication for the dcm−bacterium.

5. The method of claim 1, wherein the at least one region of identity with the genome of the *Clostridium* sp. of interest is a first region of identity and a second region of identity, and wherein the first selection marker is positioned between the first and second regions of identity.

6. The method of claim 1, wherein the *Clostridium* sp. of interest is *Clostridium beijerinckii*.

7. The method of claim 1, wherein the plasmid further comprises an origin of replication for the *Clostridium* sp. of interest.

8. The method of claim 1, wherein the first selection marker is an antibiotic resistance gene or a metabolic marker.

9. The method of claim 1, wherein the plasmid further comprises a second selection marker.

10. The method of claim 9, wherein the second selection marker is an antibiotic resistance gene or a metabolic marker.

11. A method of providing a *Clostridium* sp. with a stably integrated nucleic acid sequence of interest, which method comprises:
providing a dcm− and dam+ bacterium containing a nucleic acid molecule comprising a nucleic acid sequence of interest, wherein the nucleic acid sequence of interest comprises at least one region of identity with the genome of the *Clostridium* sp. and a first selection marker, and wherein the dcm− and dam+ bacterium and the *Clostridium* sp. are of different species, propagating the dcm− and dam+ bacterium, isolating the nucleic acid molecule from the propagated dcm− and dam+ bacterium, and transforming the *Clostridium* sp. with the isolated nucleic acid molecule.

12. The method of claim 11, wherein the dcm− and dam+ bacterium is an *E. coli* strain.

13. The method of claim 11, wherein the nucleic acid molecule further comprises an origin of replication for the dcm− and dam+ bacterium.

14. The method of claim 11, wherein the at least one region of identity with the genome of the *Clostridium* sp. is a first region of identity and a second region of identity, and wherein the first selection marker is positioned between the first and second regions of identity.

15. The method of claim 11, wherein the *Clostridum* sp. is *Clostridium beijerinckii*.

16. The method of claim 11, wherein the nucleic acid molecule further comprises an origin of replication for the *Clostridium* sp.

17. The method of claim 11, wherein the first selection marker is an antibiotic resistance gene or a metabolic marker.

18. The method of claim 11, wherein the nucleic acid molecule further comprises a second selection marker.

* * * * *